United States Patent
Donohue et al.

(10) Patent No.: US 7,647,949 B2
(45) Date of Patent: Jan. 19, 2010

(54) CO-EXTRUDED TUBING

(75) Inventors: Robert James Donohue, Clayton, NC (US); George Coggins, III, Raleigh, NC (US); Perry Benson, Benson, NC (US)

(73) Assignee: Natvar Holdings, Inc., Somerville, NJ (US)

( * ) Notice: Subject to any disclaimer, the term of this patent is extended or adjusted under 35 U.S.C. 154(b) by 0 days.

(21) Appl. No.: 11/606,269

(22) Filed: Nov. 29, 2006

(65) Prior Publication Data

US 2007/0119511 A1 May 31, 2007

Related U.S. Application Data

(63) Continuation of application No. 10/503,852, filed as application No. PCT/US2003/002019 on Jan. 23, 2003, now abandoned.

(60) Provisional application No. 60/351,916, filed on Jan. 25, 2002.

(51) Int. Cl.
*F16L 11/00* (2006.01)

(52) U.S. Cl. .................. 138/137; 137/140; 137/141; 428/36.91

(58) Field of Classification Search .............. 138/137, 138/140, 141; 428/36.9, 36.91
See application file for complete search history.

(56) References Cited

U.S. PATENT DOCUMENTS

| | | | |
|---|---|---|---|
| 4,211,741 A | 7/1980 | Ostoich | |
| 4,627,844 A | 12/1986 | Schmitt | |
| 4,948,643 A | 8/1990 | Mueller | |
| 5,404,915 A * | 4/1995 | Mugge et al. | 138/137 |
| 5,533,992 A | 7/1996 | Patel et al. | |
| 5,570,711 A | 11/1996 | Walsh | |
| 5,733,619 A | 3/1998 | Patel et al. | |
| 6,062,269 A * | 5/2000 | Tanaka et al. | 138/126 |
| 6,136,394 A | 10/2000 | Karsten | |
| 6,227,249 B1 * | 5/2001 | Akedo et al. | 138/137 |
| 6,230,749 B1 * | 5/2001 | Kertesz | 138/137 |
| 6,294,234 B1 * | 9/2001 | Kertesz | 428/34.7 |
| 6,302,151 B1 * | 10/2001 | Maitay et al. | 138/125 |
| 6,406,767 B1 | 6/2002 | Mueller | |
| 6,479,116 B1 * | 11/2002 | Small et al. | 428/36.7 |
| 6,941,975 B2 * | 9/2005 | Wilson et al. | 138/141 |
| 2002/0061377 A1 | 5/2002 | Kertesz | |

(Continued)

FOREIGN PATENT DOCUMENTS

DE 1411544 10/1969

(Continued)

OTHER PUBLICATIONS

Supplementary European Search Report issued on Sep. 26, 2008 in connection with corresponding European Appln. No. EP 03 70 5882.

*Primary Examiner*—Patrick F Brinson
(74) *Attorney, Agent, or Firm*—Lerner, David, Littenberg, Krumholz & Mentlik, LLP

(57) ABSTRACT

A co-extruded tubing for the administration of intravenous fluids has an outer layer of a polyester. An inner fluid-contact layer may be of a polyethylene or of a thermoplastic polyurethane. Where the inner fluid-contact layer is of polyethylene, an intermediate tie layer of ethylene-vinyl acetate copolymer may be included to prevent delamination.

16 Claims, 1 Drawing Sheet

U.S. PATENT DOCUMENTS

| | | |
|---|---|---|
| 2002/0139428 A1 | 10/2002 | Kertesz |
| 2002/0144744 A1 | 10/2002 | Kertesz |
| 2003/0099800 A1 | 5/2003 | Miguel et al. |

FOREIGN PATENT DOCUMENTS

| | | |
|---|---|---|
| DE | 3428191 | 2/1986 |
| EP | 1 249 336 A | 10/2002 |
| EP | 1 267 111 | 12/2002 |
| JP | 60034584 A | 5/1985 |
| JP | 1204726 A | 8/1989 |

* cited by examiner

CO-EXTRUDED TUBING

CROSS-REFERENCE TO RELATED APPLICATIONS

This is a continuation of U.S. patent application Ser. No. 10/503,852, now abandoned which is the U.S. National Stage of International Application No. PCT/US2003/002019, filed Jan. 23, 2003, which includes a claim for Convention priority based on U.S. patent application Ser. No. 60/351,916, filed Jan. 25, 2002.

FIELD OF THE INVENTION

The present invention is directed toward a co-extruded tubing for the administration of intravenous fluids that eliminates the need for the inclusion of polyvinyl chloride and plasticizers.

BACKGROUND OF RELATED TECHNOLOGY

Plastic tubings are extensively employed in the medical field, particularly for patient analysis and treatment procedures. Various FDA-approved plastics and combinations thereof are used, depending upon the specific properties the intended application demands. The selection of desired plastic materials is further limited by the use of the tubing in the in vivo treatment of human patients, as the tubing may be used in the administration of intravenous fluids or itself may be introduced into the body. Thus, numerous factors must be considered in ascertaining which materials to choose.

Polyvinyl chloride (PVC) is a material previously used to make tubing, made with suitable plasticizers necessary to enhance flexibility and other properties. However, such plasticizers or similar additives have a tendency to migrate, causing hazardous contamination with the fluid being transferred through the tubing. The contamination becomes more serious where the fluid is introduced into the body, as contamination of the blood may result. Moreover, plasticized PVC tubings have been shown to absorb nitroglycerin and insulin, and are thus unsatisfactory for the administration of these medicines. Much effort has been directed towards finding an alternative that does not suffer from the limitations of the plasticized PVC tubing.

Polyurethane has been used as an alternative to PVC in medical tubing, as in U.S. Pat. No. 4,211,741 to Ostoich. Polyurethane may be used without plasticizers and other additives, because it is a relatively soft, flexible plastic. Therefore, the possibility of the migration of additives and subsequent contamination are eliminated. In addition, polyurethane exhibits good fluid-flow characteristics. However, the high cost of polyurethane has limited its use to only extraordinary applications.

Some grades of ethylene-vinyl acetate copolymer (EVA) are currently being used as an outer layer, together with low-density polyethylene (LDPE) as an inner layer in forming composite tubing. Although this composite exhibits excellent peel strength, it lacks flexibility, clarity, and is easily scuffed or roughened. In addition, it cannot be solvent bonded. Since the tubing is the connecting link between a reservoir of fluid (nitroglycerin, insulin, etc.) and the patient, the method of connecting the tubing is an important consideration. Where, as here, solvent bonding cannot be utilized, an expensive, less reliable mechanical means of assembly is required, whereby a PVC layer must be pressure fit over the EVA-LDPE tubing to utilize the solvent-bondable characteristics of PVC. For these reasons, the EVA-LDPE product has proven to be unsatisfactory.

U.S. Pat. No. 4,627,844 to Schmitt ("Schmitt") provides a well-received alternative that includes a tri-layer tube. A commercially successful embodiment of U.S. Pat. No. 4,627,844 is sold under the trademark "SUREPATH 151" by the Plastron/Natvar Division of Tekni-Plex, Inc. As disclosed in Schmitt, an outer layer of PVC and an inner fluid-contact layer of LDPE are co-extruded with an intermediate tie layer of EVA. However, while Schmitt greatly reduces the possibility for the migration of additives from the PVC to the fluid by providing an LDPE fluid-contact layer, the elimination of the PVC is preferred.

In addition to the potential migration problem of PVC additives into a fluid being transferred within a PVC tube, PVC production, use, and disposal are the subject of many regulatory concerns, particularly in Europe. For example, steps must be taken to reduce introduction of vinyl chloride and additives into wastewater during production, and PVC must frequently be incinerated prior to introduction to a landfill. These steps are recommended to prevent introduction of PVC and other additives to the environment due to possible carcinogenic properties demonstrated by these compositions.

Therefore, there is a need for a co-extruded tubing that excludes PVC while providing the advantages of being solvent-bondable, EtO- and gamma-stable, and water-clear that may be used in the administration of nitroglycerin and insulin.

SUMMARY OF THE INVENTION

Accordingly, the present invention is a co-extruded tubing which does not include PVC. In a first embodiment, the co-extruded tubing has three layers which include an outer layer of a polyester. It also includes an inner fluid-contact layer, and an intermediate bonding layer of EVA. The inner fluid-contact layer may be of a polyethylene.

The second embodiment is a co-extruded tubing having two layers. As in the first embodiment, the co-extruded tubing includes an outer layer of a polyester, but it lacks an intermediate bonding layer. The co-extruded tubing of the second embodiment also includes an inner fluid-contact layer of a thermoplastic polyurethane.

The present invention will now be described in more complete detail with frequent reference being made to the following figures.

DETAILED DESCRIPTION OF THE INVENTION

Figure 1:
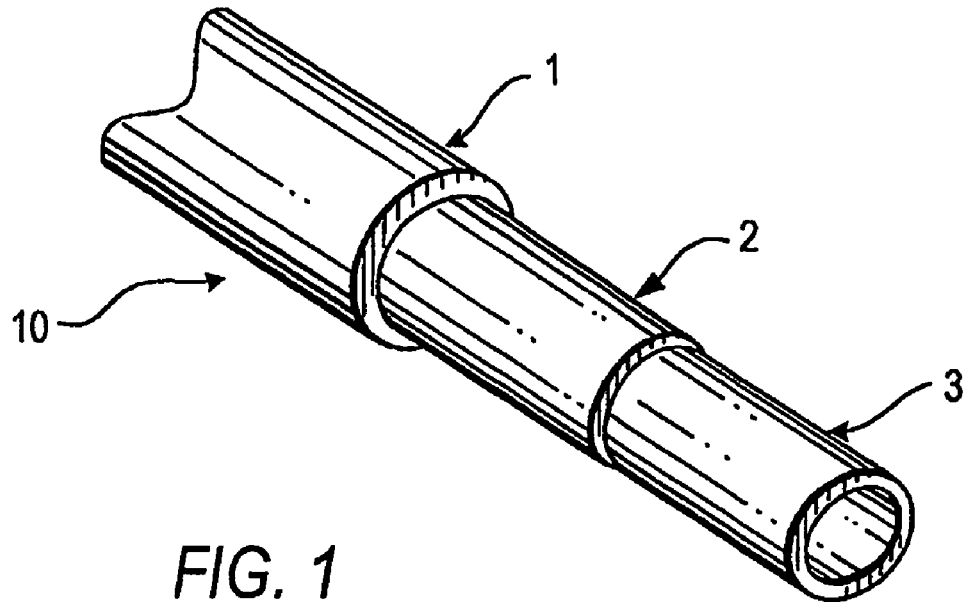
FIG. 1 is an isometric view of a tri-layered tubing of the invention with the outer layer and middle layer broken away in order to show the construction.

Referring to FIG. 1, one aspect of the present invention provides a co-extruded tri-layer tubing 10 that includes an outer layer 1 of a polyester, such as a copolyester thermoplastic elastomer (TPE), an inner fluid-contact layer 3, and an intermediate bonding layer 2 of EVA.

Figure 2:
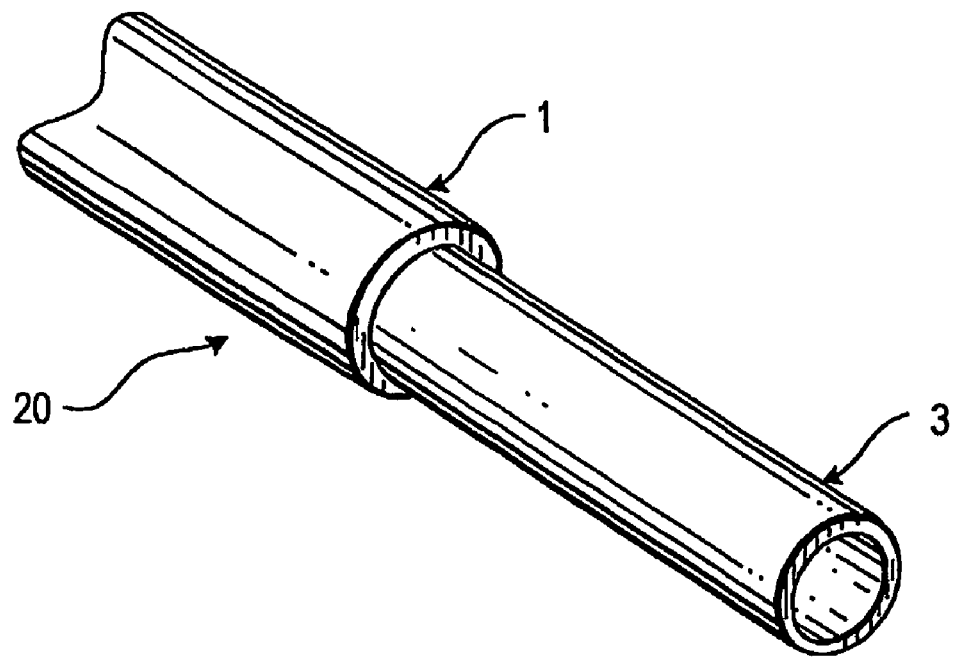
FIG. 2 is an isometric view of a dual-layered tubing of the invention with the outer layer broken away in order to show the construction.

Referring to FIG. 2, another aspect of the present invention provides a dual-layer tubing 20 that eliminates the need for an intermediate bonding layer. This dual-layer tubing 20 includes an outer layer 1 of a polyester, such as a copolyester thermoplastic elastomer (TPE), and an inner fluid-contact layer 3 of a thermoplastic polyurethane (TPU), such as an aromatic or aliphatic polyether-based TPU.

The polyester outer layer 1 has unexpectedly provided a tubing that is water-clear and flexible without the addition of plasticizers and other additives. The polyester may be a copolyester ether TPE such as Ecdel Elastomer 9966, Ecdel Elastomer 9965, Ecdel Elastomer 9967, and Ecdel development polymer 24569 available from Eastman Chemical. These are copolyesters of alternating hard poly-1,4-butanediol terephthalate and soft long-chain polyalkylene ether terephthalate block copolymers connected by ester and ether linkages. The thickness of the polyester outer layer 1 may be from about 0.001 in. (0.025 mm) to about 0.006 in. (0.152 mm).

The inner layer 3 provides a fluid-contact surface. The inner layer 3 may be either a polyethylene or a thermoplastic polyurethane elastomer (TPU). The thickness of the inner layer 3 may be from about 0.001 in. (0.025 mm) to about 0.030 in. (0.762 mm).

If the inner layer 3 is chosen to be a polyethylene, a variety of polyethylene materials are suitable. For example, polyethylene may be either a branched low-density polyethylene (LDPE), such as 808 Eastman LDPE, available from Eastman Chemical, or a linear high-density polyethylene (HDPE), such as 9506 Chevron HDPE, 9406 Chevron HDPE, and 9503 Chevron HDPE, available from Chevron Corporation.

Alternatively, a thermoplastic polyurethane elastomer (TPU) may be used as the inner fluid-contact layer 3. Generally, a TPU is the reaction product of a polyol and isocyanate and usually includes a combination of hard and soft segment domains. An aromatic polyether-based TPU or an aliphatic polyether-based TPU is desirable for use with the present invention. Useful TPU's include the Pellethane 2363-80 AE series available from Dow Chemical Company and the Tecothane series and the Tecoflex series available from Thermedics Polymer Products, a division of VIASYS Healthcare.

If a polyethylene is selected as the inner fluid-contact layer 3, it is desirable to include an intermediate tie layer 2 to prevent delamination. The tie layer or bonding layer 2 is not necessary if the inner layer 3 is chosen to be a TPU. The intermediate bonding layer 2 may be ethylene-vinyl acetate copolymer (EVA). A vinyl acetate content of the EVA of approximately 28% allows for maximum flexibility without losing the desired extrusion characteristics. One suitable EVA copolymer available from Equistar Chemical is UE 634-006. The thickness of the bonding layer 2 may be from about 0.001 in. (0.025 mm) to about 0.006 in. (0.152 mm).

The respective thickness of each layer of tubing 10,20 can be controlled by the extrusion tooling utilized, such as the "Tri Die" extrusion apparatus manufactured by the Genca Division of General Cable Company, Clearwater, Fla. This provides a uniform thickness of the layers both of the tri-layer tubing, including three layers 1,2,3, and of the dual-layer tubing including two layers 1,2, which are co-extruded as is well-known in the art, resulting in the tri-layer tubing 10 and/or the dual-layer tubing 20 of the present invention.

The tubing of the subject invention has the advantages of not only being water-clear and flexible in the absence of PVC, but also is EtO- and gamma-stable. The tubing maintains its integrity (delamination does not occur) and clarity upon ethylene oxide (EtO) and gamma irradiation sterilization processes. Another major advantage is that the tubing demonstrates solvent-bonding capability similar to that of PVC.

While there have been described what are presently believed to be the preferred embodiments of the invention, those skilled in the art will realize that changes and modifications may be made thereto without departing from the spirit of the invention, and it is intended to include all such changes and modifications as fall within the true scope of the invention.

What is claimed is:

1. A co-extruded tubing for the transfer of fluids, said tubing having at least two layers comprising:
   an outer layer, said outer layer comprising a polyester; and
   an inner fluid-contacting layer comprising:
   a thermoplastic polyurethane elastomer.

2. A co-extruded tubing as claimed in claim 1 wherein said polyester is a copolyester thermoplastic elastomer.

3. A co-extruded tubing as claimed in claim 2 wherein said polyester is a copolyester thermoplastic elastomer is a polyester ether thermoplastic elastomer.

4. A co-extruded tubing as claimed in claim 3 wherein said copolyester ether thermoplastic elastomer is a copolyester of alternating hard poly-1,4-butanediol terephthalate and soft long-chain polyalkylene ether terephthalate block copolymers connected by ester and ether linkages.

5. A co-extruded tubing as claimed in claim 1 wherein said outer layer has a thickness in a range from about 0.025 mm to about 0.152 mm.

6. A co-extruded tubing as claimed in claim 1 wherein said thermoplastic polyurethane elastomer is an aromatic polyether-based thermoplastic polyurethane elastomer.

7. A co-extruded tubing as claimed in claim 1 wherein said thermoplastic polyurethane elastomer is an aliphatic polyether-based thermoplastic polyurethane elastomer.

8. A co-extruded tubing as claimed in claim 1 wherein said inner fluid-contacting layer has a thickness in a range from about 0.025 mm to about 0.762 mm.

9. A co-extruded tubing for the transfer of fluids, said tubing having at least three layers comprising:
   an outer layer, said outer layer comprising a polyester;
   an inner fluid-contacting layer comprising a polyethylene; and
   an intermediate bonding layer between said outer layer and said inner fluid-contacting layer, said intermediate bonding layer comprising an ethylene-vinyl acetate copolymer.

10. A co-extruded tubing as claimed in claim 9 wherein said polyester is a copolyester thermoplastic elastomer (TPE).

11. A co-extruded tubing as claimed in claim 10 wherein said copolyester thermoplastic elastomer is a copolyester ether thermoplastic elastomer.

12. A co-extruded tubing as claimed in claim 9 wherein said polyethylene is a branched low-density polyethylene.

13. A co-extruded tubing as claimed in clam 9 wherein said polyethylene is a linear high-density polyethylene.

14. A co-extruded tubing as claimed in claim 9 wherein said intermediate bonding layer is an ethylene-vinyl acetate copolymer having a vinyl acetate content of about 28%.

15. A co-extruded tubing as claimed in claim 9 wherein said intermediate bonding layer has a thickness in a range from about 0.025 mm to about 0.152 mm.

16. A co-extruded tubing for the transfer of fluids, said tubing having at least two layers comprising:
   an outer layer, said outer layer comprising a polyester comprising a copolyester thermoplastic elastomer comprising a copolyester ether thermoplastic elastomer comprising a copolyester of alternating hard poly-1,4-butanediol terephthalate and soft long-chain polyalkylene ether therephthalate block copolymers connected by ester and ether linkages; and
   an inner fluid-contacting layer.

* * * * *